US009828316B2

(12) United States Patent
Sharratt et al.

(10) Patent No.: US 9,828,316 B2
(45) Date of Patent: Nov. 28, 2017

(54) PROCESS FOR PURIFYING (HYDRO)HALOCARBON COMPOSITIONS

(71) Applicant: MEXICHEM AMANCO HOLDING S.A. DE C.V., Tlalnepantla (MX)

(72) Inventors: Andrew Sharratt, Cheshire (GB); John Hayes, Cheshire (GB); Claire Rees, Cheshire (GB)

(73) Assignee: MEXICHEM AMANCO HOLDINGS S.A. de C.V., Tlalnepantla (MX)

( * ) Notice: Subject to any disclaimer, the term of this patent is extended or adjusted under 35 U.S.C. 154(b) by 0 days.

(21) Appl. No.: 14/786,318

(22) PCT Filed: Apr. 23, 2014

(86) PCT No.: PCT/GB2014/051259
§ 371 (c)(1),
(2) Date: Oct. 22, 2015

(87) PCT Pub. No.: WO2014/174281
PCT Pub. Date: Oct. 30, 2014

(65) Prior Publication Data
US 2016/0060192 A1    Mar. 3, 2016

(30) Foreign Application Priority Data
Apr. 23, 2013 (GB) .................................. 1307327.5

(51) Int. Cl.
| C07C 17/389 | (2006.01) |
| C09K 3/30 | (2006.01) |
| C09K 5/04 | (2006.01) |
| A61K 9/12 | (2006.01) |
| A62D 1/00 | (2006.01) |
| C07C 17/383 | (2006.01) |
| C07C 19/08 | (2006.01) |
| C08J 9/14 | (2006.01) |

(52) U.S. Cl.
CPC ............ *C07C 17/389* (2013.01); *A61K 9/124* (2013.01); *A62D 1/00* (2013.01); *C07C 17/383* (2013.01); *C07C 19/08* (2013.01); *C08J 9/146* (2013.01); *C09K 3/30* (2013.01); *C09K 5/044* (2013.01); *C09K 5/045* (2013.01); *C09K 2205/122* (2013.01); *C09K 2205/24* (2013.01)

(58) Field of Classification Search
CPC .................................................. C07C 17/389
See application file for complete search history.

(56) References Cited

U.S. PATENT DOCUMENTS

| 3,865,887 A | 2/1975 | Gordon |
| 4,906,796 A | 3/1990 | Yates |
| 4,940,824 A | 7/1990 | Yates |
| 5,164,355 A * | 11/1992 | Farris .................... C01B 31/085 |
| | | 502/416 |
| 5,396,001 A | 3/1995 | Pennetreau |
| 5,514,633 A | 5/1996 | Noguchi et al. |
| 5,523,499 A | 6/1996 | Corbin et al. |
| 5,536,891 A | 7/1996 | Beard, Jr. |
| 7,084,316 B2 | 8/2006 | Ohno et al. |
| 7,384,519 B2 | 6/2008 | Cottrell et al. |
| 7,696,392 B2 * | 4/2010 | Ohno ........................ B01J 23/26 |
| | | 570/179 |
| 7,829,058 B2 * | 11/2010 | Hoos ....................... B01D 15/00 |
| | | 423/490 |
| 2003/0157009 A1 | 8/2003 | Corr et al. |
| 2005/0124834 A1 | 6/2005 | Ohno et al. |
| 2005/0133360 A1 | 6/2005 | Cottrell |
| 2008/0011159 A1 | 1/2008 | Thomas et al. |

FOREIGN PATENT DOCUMENTS

| CN | 1827566 | 9/2006 |
| CN | 101012146 | 8/2007 |
| CN | 102101822 | 6/2011 |
| CN | 102101823 | 6/2011 |
| KR | 0159176 | 1/1999 |
| WO | WO98/19982 | 5/1998 |
| WO | WO2004/052264 | 6/2004 |
| WO | WO2004/074225 | 9/2004 |
| WO | WO2005/044765 | 5/2005 |
| WO | WO2007/144632 | 12/2007 |

OTHER PUBLICATIONS

Falcon (Material Safety Data Sheet 152a; Oct. 30, 2006; pp. 1-5).*
KR0159176, Jan. 15, 1999; English Abstract, pp. 1.*
Bernal, E. Advances in Gas Chromatography 2014, pp. 1-26.*
International Search Report; PCT/GB2014/051259; Apr. 23, 2014.
Written Opinion of the international Searching Authority: PCT/GB2014/051259; Apr. 23, 2014.
UK Search Report issued on GB Application No. 1307327.5 dated Dec. 18, 2013.
Bellpearl Presentation, May 12, 2012.
Foley, H., "Carbogenic molecular sieves: synthesis, properties and applications." Microporous Materials, 4, 1995, 407-433.
Green, Introducing . . . Carbon Molecular Sieve, http://hengyeusa.com, printed Nov. 2, 2013.
Koresh et al., "Study of Molecular Sieve Carbons." J.C.S. Faraday I, 76, 1980, 2472-2484.
Lemus et al., "Removal of chlorinated organic volatile compounds by gas phase adsorption with activated carbon." Chemical Engineering Journal, 211-212, 2012, 246-253.

(Continued)

*Primary Examiner* — Jafar Parsa
*Assistant Examiner* — Medhanit Bahta
(74) *Attorney, Agent, or Firm* — Ryan Kromholz & Manion, S.C.

(57) ABSTRACT

A process for treating a composition comprising one or more desired (hydro)halocarbons and one or more undesired halogenated hydrocarbon containing impurities so as to reduce the concentration of at least one undesired halogenated hydrocarbon containing impurity, the process comprising contacting the composition with an adsorbent comprising a carbon molecular sieve.

38 Claims, No Drawings

(56) References Cited

OTHER PUBLICATIONS

Mariwala et al., "Adsorption of halocarbons on a carbon molecular sieve," Microporous and Mesoporous Materials, 22, 1998, 281-288.
Mieville et al., Carbon Molecular Sieves and Other Porous Carbons, Mega-Carbon Company, downloaded from citeseerx.ist.psu.edu, on Mar. 14, 2016.
Reid et al., "Adsorption Kinetics and Size Exclusion Properties of Probe Molecules . . . " J. Phys. Chem. B, 105, 2001, 10619-10628.
Vaduva et al., "Carbon Molecular Sieves Production and Performance Assessment in $CO_2$ Separation by Selective Adsorption." U.P.B. Sci. Bull., Series B, 69(3), 2007, 95-106.

\* cited by examiner

PROCESS FOR PURIFYING (HYDRO)HALOCARBON COMPOSITIONS

This invention relates to a process for reducing the concentration of undesired impurities and, preferably, of undesired halogenated organic compounds in (hydro)halocarbon compositions.

(Hydro)halocarbons are typically used as refrigerant or propellant materials. Over the last 20 years, the variety of (hydro)halocarbons used in these applications has changed as it has been discovered that some such materials (such as difluorodichloromethane, R12) deplete the earth's ozone layer, while others (such as chlorodifluoromethane, R134a) have an unacceptably high action as a greenhouse gas.

The nature of the manufacturing processes of halogenated hydrocarbons is such that one or more undesired or peripheral products are produced alongside a desired product in a product composition. The desired product is then separated from the undesired or peripheral products by, say, distillation.

However, even after distillation, a desired product often includes trace quantities of the undesired or peripheral products, for example as a result of the formation of an azeotropic mixture. It is also possible that substances used in other parts of the manufacturing process may contaminate the product in trace quantities. Other separation techniques may also leave trace quantities of impurities in the desired composition.

While in certain circumstances, such trace level contamination does not significantly affect the end use of the desired product, in others, such as where the contaminant is toxic or has a relatively high global warming potential, where the end product may come into contact with materials which may be degraded by the contaminant or where the end product is for use in food or personal products, it is desirable to further reduce or eliminate the presence of those contaminants. It is particularly desirable to control the content of low-level impurities in compositions intended for use in the medical and/or pharmaceutical field, such as those intended for use as a medical grade propellant.

It is known to use zeolites as molecular sieves to remove contaminant materials from (hydro)halocarbon products. US2005/0133360 describes the use of zeolites to purify 1,1,1,2-tetrafluoroethane (HFC-134a) and chlorodifluoromethane (HCFC-22). WO2004/074225 describes the use of zeolites for the removal of sulphur containing impurities from (hydro)halocarbons.

Zeolites provide a useful and effective means for separating components of a mixture when those components are of substantially different shapes and/or sizes. However, there is a need for a method and means for removing impurities from a (hydro)halocarbon composition which is effective when the undesired or peripheral component is of a similar shape and/or size to the desired component.

The listing or discussion of an apparently prior-published document in this specification should not necessarily be taken as an acknowledgement that the document is part of the state of the art or is common general knowledge According to a first aspect of the invention, there is provided a process for treating a composition comprising one or more desired (hydro)halocarbons and one or more undesired halogenated hydrocarbon containing impurities so as to reduce the concentration of at least one undesired halogenated hydrocarbon containing impurity, the process comprising contacting the composition with an adsorbent comprising a carbon molecular sieve.

The inventors have surprisingly found that the use of carbon molecular sieves in the purification of (hydro)halocarbons provides for highly selective removal of halogenated hydrocarbon impurities. The invention provides a marked improvement in such performance when compared with the use of other molecular sieves having pore sizes of a similar order.

The contacting step of the process may be conducted in either the liquid or the vapour phase, but the liquid phase is preferred as it is more economical to run.

Of course, the contacting step of the process should be conducted at a temperature that allows absorption to occur. The process preferably is performed, at least in part, at a temperature of less than about 200° C., such as from about 5° C. to about 200° C. In some preferred embodiments, the process is performed, at least in part, at a temperature of about 20° C. to about 100° C. In still further preferred embodiments, the process is performed, at least in part, at a temperature of about 20° C. to about 60° C., e.g. around 40° C.

The contacting step of the method of the present invention may be conducted at any pressure sufficient to keep the components of the composition in the liquid or vapour phase, as appropriate. If the process is conducted in the liquid phase, it is preferably conducted at its autogeneous pressure, i.e. the pressure that the liquid itself exerts, or higher if desired. If the process is conducted in the vapour phase, it is preferably conducted at a pressure of from 0.1 MPa to the saturation pressure. For a given temperature, the saturation pressure of a pure component is that pressure at which vaporisation of the liquid takes place.

In some preferred embodiments, the process further comprises an adsorbent treatment step prior to the contacting step. Preferably, the adsorbent treatment step comprises heating the adsorbent to a maximum temperature of at least 150° C., for example at least 200° C., at least 250° C., at least 300° C., at least 350° C. or at least 400° C.

In some embodiments, the adsorbent treatment step comprises heating the adsorbent to the or a maximum temperature at a rate of 1° C./min to 100° C./min. Preferably, the adsorbent treatment step comprises heating the adsorbent to the or a maximum temperature at a rate of 10° C./min to 60° C./min. Preferably, the adsorbent treatment step comprises heating the adsorbent to the or a maximum temperature at a rate of 15° C./min to 40° C./min, e.g. around 20° C./min.

Preferably, the adsorbent treatment step is sufficiently long in duration to ensure that any adsorbed species present on or in the adsorbent prior to use are removed. For example, the adsorbent treatment step may include maintaining the adsorbent at or around the or a maximum temperature for between 1 second and 1 hour.

In some embodiments, the adsorbent treatment step comprises exposing the adsorbent to one or more inert gases, e.g. $N_2$ or one or more noble gases. In some embodiments, the exposure is performed before, during or after the or a heat treatment step. Preferably, the exposure is performed during at least part of the heat treatment step.

Preferably, the adsorbent has a mean pore diameter of around 0.5 Å to around 20 Å, e.g. around 1 Å to around 10 Å. The pores may be spherical or elliptical. In the case of elliptical pores the diameter may refer to either dimension.

The process typically can be used to treat any (hydro)halocarbon that is made by any method.

By the term "(hydro)halocarbon" we mean a compound that contains carbon, one or more halogen atoms and, optionally, hydrogen and/or oxygen. The (hydro)halocarbon may be saturated or unsaturated. Preferably, the (hydro) halocarbon has a carbon chain length of from one to four.

By the term "(hydro)haloethane" we mean a compound that contains two carbon atoms, one or more halogen atoms and, optionally, hydrogen.

The composition to be treated may comprise one or more desired (hydro)halocarbons selected from halogenated alkanes, halogenated alkenes and halogenated ethers.

Preferably, the composition to be treated comprises at least one desired (hydro)halocarbon selected from hydrofluoroalkanes, hydrochlorofluoroalkanes, chlorofluoroalkanes, perfluoroalkanes, perchloroalkenes, hydrochloroalkenes and (hydro)fluoroethers. The process of the invention is particularly suitable for treating compositions in which the or each desired (hydro)halocarbon contains fluorine atoms as the only halogen atoms, for example hydrofluoroalkanes, perfluoroalkanes and/or (hydro)fluoroethers. It is particularly preferred that the or each desired compound is a hydrofluoroalkane.

By the term "hydrofluoroalkane", we mean an alkane which contains only carbon, hydrogen and fluorine atoms.

By the term "hydrochlorofluoroalkane", we mean an alkane which contains only carbon, chlorine, fluorine and hydrogen atoms.

By the term "chlorofluoroalkane", we mean an alkane which contains only carbon, chlorine and fluorine atoms.

By the term "perfluoroalkane", we mean an alkane which contains only carbon and fluorine atoms.

By the term "perchloroalkene", we mean an alkene which contains only carbon and chlorine atoms.

By the term "hydrochloroalkene", we mean an alkene which contains only carbon, hydrogen and chlorine atoms.

By the term "(hydro)fluoroether", we mean an ether which contains carbon, fluorine and oxygen atoms and, optionally, hydrogen atoms.

Desired hydrofluoroalkanes that may be purified include 1,1,1,2-tetrafluoroethane (R-134a), 1,1-difluoroethane (R-152a), 1,1,1-trifluoroethane (R-143a) or other mono-, di-, tri- or tetra-fluoroethanes. The use of the process of the present invention to purify 1,1-difluoroethane (R-152a) is particularly preferred.

Desired hydrochlorofluoroalkanes that may be purified include 1,1-dichloro-1-fluoroethane (R-141b), 1-chloro-1,1-difluoroethane (R-142b), 1,1,1-trifluoro-2-chloroethane (R-133a), 2,2-dichloro-1,1,1-trifluoroethane (R-123), 2-chloro-1,1,1,2-tetrafluoroethane (R-124) or other hydrochlorofluoroethanes.

Desired chlorofluoroalkanes that may be purified include 1,2-dichloro-1,1,2,2-tetrafluoroethane (R-114) and 1,1,1-trichloro-2,2,2-trifluoroethane (R-113a) or other chlorofluoroethanes.

Desired perfluoroalkanes that may be purified include perfluoroethane (R-116).

The process can also reduce the concentration of inorganic and/or organic sulphur containing impurities. It is particularly advantageous to use the process to reduce the concentration of organic sulphur containing impurities because these are typically more difficult to remove using standard techniques known to those skilled in the art.

By the term "organic sulphur containing impurities", we mean compounds containing at least carbon and sulphur, optionally including other atoms such as hydrogen and oxygen. Organic sulphur containing impurities that can be removed/reduced include (but are not limited to) dimethyldisulphide, ethanethiol, diethyldisulphide, carbon disulphide and carbonyl sulphide.

By the term "inorganic sulphur containing impurities", we mean compounds containing at least sulphur, optionally including other atoms such as hydrogen and oxygen. Inorganic sulphur containing impurities that can be removed/reduced include (but are not limited to) hydrogen sulphide, sulphur dioxide, sulphur trioxide and/or sulphuric acid.

The process of the present invention can be used to remove or reduce the concentration of one or more undesired halogenated organic compounds. The process is particularly suitable for the removal/reduction of halogenated organic compounds containing one or two carbon atoms, although other undesired halogenated organic compounds may also be removed. When the undesired halogenated organic compounds contain two or more carbon atoms, they may be saturated or unsaturated.

By the term "undesired halogenated organic compounds" we mean undesired compounds that contain carbon, one or more halogen atoms and, optionally, hydrogen. The undesired halogenated organic compounds preferably contain fluorine and/or chlorine and/or bromine, more preferably fluorine and/or chlorine. Preferably, the undesired halogenated organic compounds comprise halogenated methanes, for example halomethanes, dihalomethanes or trihalomethanes.

The process typically removes at least 50% by weight, more preferably at least 90% by weight and even more preferably at least 98% by weight of the halogenated hydrocarbon impurities. In some embodiments, the process reduces the concentration of halogenated hydrocarbon impurities to levels at, around or below the limit of detection by smell and/or by gas chromatography.

The process does not necessarily reduce the concentration of every one of the one or more undesired halogenated hydrocarbon impurities, but it may do so.

Halogenated organic compounds that may be removed/reduced using the process of the present invention include (but are not limited to) chlorofluoromethanes, e.g chlorodifluoromethane (R-22) and chlorofluoromethane (R-31).

By the term "carbon molecular sieve", we mean a molecular sieve comprising a substantially amorphous carbonaceous adsorbent with substantially uniform nanopores preferably of smaller than 20 angstrom in mean pore diameter, such as those carbonaceous adsorbents produced by pyrolysis of polymeric precursor materials. As is understood by those skilled in art, such materials are distinct from activated carbon, which is typically produced from vegetable materials such as coconut husks and typically exhibits a far greater range of pore sizes.

If required, the adsorbent may be dried before use. Alternatively, the adsorbent may be used in the form it is obtained from the manufacturer. The preferred moisture level is less than about 1.5% by weight.

Typically, the process is conducted by circulating the composition to be treated through a polishing bed containing the adsorbent. The polishing bed may be a packed or fluidised bed, although a packed bed is preferred.

The contact time depends on the amount of adsorbent being used and on its freshness. The skilled person would readily be able to determine a suitable contact time for a particular process.

The effectiveness of the adsorbent used in the process will deteriorate with time. The time that it takes for the adsorbent to deteriorate depends on a number of factors, such as the ratio of the amount of adsorbent to the amount of the composition being treated.

The process of the present invention may further comprise the step of regenerating the adsorbent after it has been contacted with the (hydro)halocarbon composition. For example, the adsorbent may be regenerated by contacting it with a heated nitrogen stream or by heating it whilst nitrogen is passed over it.

It should be appreciated that a composition to be treated may be contacted with the adsorbent more than once. In such a process, the composition may be subjected to repeated contacts with one type of adsorbent or subjected to contacts with more than one type of adsorbent. Repeated contact will further reduce the content of the one or more undesired sulphur containing impurities and, if appropriate, of the one or more undesired halogenated organic compounds.

Typically, the composition to be treated may be contacted with the adsorbent as many times as necessary to remove a sufficient quantity of the undesired halogenated hydrocarbons. The number of times that a composition is contacted with the adsorbent depends on a number of factors, such as the freshness of the adsorbent and the initial level of impurities.

Typically, it is not necessary to subject the (hydro)halocarbon composition to any additional treatment(s) prior to or after the process of the present invention in order to ensure that the concentration of halogenated hydrocarbon impurities is reduced.

However, if desired, the process can include one or more additional purifying steps, which may be conducted before and/or after the process of the present invention. The additional purifying steps may reduce the concentration of undesired halogenated hydrocarbon impurities that are reduced/removed by the adsorbent.

The additional purifying steps may, optionally, reduce the concentration of other undesired compounds, such as water or sulphur containing compounds.

Any methods of purifying (hydro)halocarbons known in the art may be used as additional purifying steps. For example, treatment with other molecular sieves (e.g. zeolites) which are preferably acid stable molecular sieves and may have a pore size of from 2 to 10 Å are preferred. Additionally or alternatively, drying agents and/or distillation techniques may be used.

Layers of different adsorbents and/or drying agents can be combined within a single polishing bed. The order of the layers can be selected by a person skilled in the art so as to provide the most efficient treatment.

If required, distillation can be conducted before and/or after the composition to be treated is contacted with the adsorbent(s) and/or drying agent(s) in the polishing bed.

According to another aspect of the invention, there is provided the use of an adsorbent comprising a carbon molecular sieve to reduce the concentration of at least one undesired halogenated hydrocarbon impurity in a (hydro)halocarbon composition, such as those defined above.

According to yet another aspect of the present invention, there is provided a composition that is substantially free of undesired halogenated hydrocarbon impurities obtainable by a process as described above.

Preferably, the composition is 1,1-difluoroethane (R-152a) or 1,1,1,2-tetrafluoroethane (R-134a) or mixtures thereof that is substantially free of undesired halogenated hydrocarbon impurities.

By the phrase "substantially free of undesired halogenated hydrocarbon impurities", we mean that the undesired halogenated hydrocarbon impurities are present in an amount that is less than that which results in a quantity at around or below the amount detectable by gas chromatography. The skilled person will appreciate that the exact amount of undesired halogenated hydrocarbon impurities will depend on which halogenated hydrocarbon impurities were present in the composition before the process is conducted because different compounds may be detectable at different levels using gas chromatography. In some embodiments, "substantially free" refers to an impurity being present in a concentration of less than 15 ppm.

Compositions obtainable by a process as described above may be used as a propellant, especially as a medical and/or pharmaceutical propellant. Halogenated alkanes, such as hydrofluoroalkanes, for example 1,1-difluoroethane (R-152a) and 1,1,1,2-tetrafluoroethane (R-134a) and mixtures thereof are suitable for this use.

Accordingly, in another aspect, the invention provides a pharmaceutical delivery device containing one or more pharmaceutically active substances and/or compositions and a composition obtainable by the methods described above.

Compositions obtainable by a process as described above may also be used as a refrigerant, as a foam blowing agent, as a solvent and/or as a fire extinguishing agent.

For example, 1,1,1,2-tetrafluoroethane (R-134a) obtainable by a process as described above may be used as a solvent, for example as an extraction solvent for natural products, preferably as a flavour and/or fragrance extraction solvent.

In a further aspect, the invention provides an apparatus comprising a carbon molecular sieve and means to supply to said carbon molecular sieve a composition comprising one or more desired (hydro)halocarbons and one or more undesired halogenated hydrocarbon containing impurities so as to reduce the concentration of at least one undesired halogenated hydrocarbon containing impurity, wherein the undesired halogenated hydrocarbon containing impurities comprises one or more of a mono-, di- or trihalomethane, the desired (hydro)halocarbons are selected from (i) 1,1,1,2-tetrafluoroethane, 1,1,1-trifluoroethane, 1,1-difluoroethane, perfluoroethane or other mono-, di-, tri- or tetrafluoroethanes;

(ii) 1,2-dichloro-1,1,2,2-tetrafluoroethane, 1,1,1-trichloro-2,2,2-trifluoroethane, 1,1-dichloro-1-fluoroethane, 1-chloro-1,1-difluoroethane, 1,1,1-trifluoro-2-chloroethane, 2,2-dichloro-1,1,1-trifluoroethane (R-123), 2-chloro-1,1,1,2-tetrafluoroethane and/or other (hydro)chlorofluoroethanes; and/or (iii) (hydro)chloroethanes, (hydro)bromoethanes and/or (hydro)iodomethanes, the apparatus being adapted and arranged to perform a process as described above.

In a further aspect, the invention provides a method of providing cooling or heating using a heat transfer fluid comprising:

(i) 1,1,1,2-tetrafluoroethane, 1,1,1-trifluoroethane, 1,1-difluoroethane, perfluoroethane or other mono-, di-, tri- or tetrafluoroethanes;

(ii) 1,2-dichloro-1,1,2,2-tetrafluoroethane, 1,1,1-trichloro-2,2,2-trifluoroethane, 1,1-dichloro-1-fluoroethane, 1-chloro-1,1-difluoroethane, 1,1,1-trifluoro-2-chloroethane, 2,2-dichloro-1,1,1-trifluoroethane (R-123), 2-chloro-1,1,1,2-tetrafluoroethane and/or other (hydro)chlorofluoroethanes; and/or (iii) (hydro)chloroethanes, (hydro)bromoethanes and/or (hydro)iodomethanes;

which method comprises a method of removing an undesired halogenated hydrocarbon as described above. Preferably, the method of providing cooling is performed in a mobile air conditioning system.

In another aspect, the invention provides a heat transfer device comprising a heat transfer fluid comprising:

(i) 1,1,1,2-tetrafluorethane, 1,1,1-trifluoroethane, 1,1-difluoroethane, perfluoroethane or other mono-, di-, tri- or tetrafluoroethanes;

(ii) 1,2-dichloro-1,1,2,2-tetrafluoroethane, 1,1,1-trichloro-2,2,2-trifluoroethane, 1,1-dichloro-1-fluoroethane, 1-chloro-1,1-difluoroethane, 1,1,1-trifluoro-2-chloroethane, 2,2-dichloro-1,1,1-trifluoroethane (R-123), 2-chloro-1,1,2-tetrafluoroethane and/or other (hydro)chlorofluoroethanes; and/or (iii) (hydro)chloroethanes, (hydro)bromoethanes and/or (hydro)iodomethanes;

and an absorbent comprising a carbon molecular sieve. Preferably, the heat transfer device is a refrigeration system.

The present invention is now illustrated but not limited by the following Examples.

EXAMPLE 1

A small sample (approximately 50 mg) of each adsorbent was accurately weighed into a 100 μl alumina crucible. The adsorbent was first pre-treated by heating from 30-350° C. at 20° C./min under flowing nitrogen (125 ml/min). The sample was then cooled to 40° C. and exposed to 16.67% v/v HFC-152a in nitrogen for 2 hours with any uptake being monitored gravimetrically. Any adsorbent that showed negligible capacity for HFC-152a was then further screened for methyl chloride adsorption in the same manner.

The results are shown in Table 1, below.

The HFC-152a was of industrial grade and was sourced from Du Pont. This material was analysed and found to have the following composition:

| | |
|---|---|
| Methyl Chloride = | 28 ppm |
| Unknown 1 = | 5 ppm |
| 254fb (CF$_3$CH$_2$CH$_2$F) = | 7 ppm |
| E-1131 (CHF═CHCl) = | 1.2 ppm |
| Balance HFC-152a (99.9588%) | |

COMPARATIVE EXAMPLES 1 TO 7

Various zeolite molecular sieves and a sample of activated carbon was treated in the same manner as the carbon molecular sieve of Example 1 and was exposed to HFC-152a in nitrogen in the same manner as in Example 1, with any uptake being monitored gravimetrically. The adsorbent was then further screened for methyl chloride adsorption in the same manner.

The results are shown in Table 1, below.

TABLE 1

| | | Capacity (% wt) | |
|---|---|---|---|
| Example | Adsorbent | Methyl Chloride | HFC-152a |
| Comparative Example 1 | Chemviron 207ea | — | 17.53 |
| Comparative Example 2 | UOP AW300 | — | 2.11 |
| Comparative Example 3 | UOP AW500 | — | 2.84 |
| Comparative Example 4 | TOSOH 4A | — | 3.81 |
| Comparative Example 5 | Sigma 3A | — | 2.36 |
| Comparative Example 6 | Sigma 4A | — | 2.98 |
| Comparative Example 7 | Sigma 5A | — | 18.37 |
| Example 1 | Union Showa Carbon Molecular Sieve (CMS) | 11.89 | 0.28 |

As can be seen from Table 1, the zeolite and activated carbon adsorbents of Comparative Examples 1 to 7 were found to adsorb HFC-152a (some in significant quantities). Surprisingly, the carbon molecular sieve of Example 1 adsorbed little HFC-152a but selectively adsorbed methyl chloride.

EXAMPLE 2

A 30 g sample of HFC-152a containing 28 ppm methyl chloride was prepared. This sample was treated with 0.5 g Union Showa carbon molecular sieve in a glass pressure cylinder at room temperature and autogenous pressure while being agitated with a magnetic stirrer. After 8 hours of contact time, a sample of liquid HFC-152a was removed for analysis by gas chromatography. The residual methyl chloride was measured at 9 ppm.

EXAMPLES 3 TO 4

A small sample (approximately 35 mg) of each adsorbent was accurately weighed into a 100 μl alumina crucible. The adsorbent was first equilibrated at 30° C. under nitrogen (100 ml/min) for 5 minutes, then pre-treated by heating from 30-350° C. at 20° C./min under flowing nitrogen (100 ml/min) and held at 350° C. for 5 minutes. The sample was then cooled to 40° C. at −20° C./min, equilibrated under nitrogen (40 ml/min) for 23.8 minutes and exposed to 16.67% v/v HFC-152a (60 ml/min) in nitrogen for 2 hours.

The supplied HFC-152a was in Examples 3 to 4 found to have a methyl chloride concentration of 24 ppm. Uptake of HFC-152a and methyl chloride to the absorbents was measured by thermogravimetric analysis. The results are shown in Table 2.

TABLE 2

| | | Capacity (% wt) | |
|---|---|---|---|
| Example | Adsorbent | Methyl Chloride | HFC-152a |
| Example 3 | Union Showa CMS | 13.33 | 0.05 |
| Example 4 | Carboxen 569 | 10.79 | 3.56 |

EXAMPLES 5 TO 7

Samples of the absorbents were dried in a chamber furnace at 350° C. for 12 h under nitrogen. 0.5000 g of the dried absorbents were then placed into pressure vessels containing magnetic stirrer bars. Approximately 40 ml HFC-152a was added to each pressure vessel, which was sealed and stirred at 1000 rpm for 7 hours.

The supplied HFC-152a was in Examples 3 to 4 found to have a methyl chloride concentration of 24 ppm. The residual quantity of methyl chloride in the remaining HFC-152a was measured by gas chromatography. The results are shown in Table 3.

TABLE 3

| Example | Absorbent | Residual MeCl (ppm) |
|---|---|---|
| Example 5 | Union Showa CMS | 12 |
| Example 6 | Carboxen 569 | 10 |
| Example 7 | Carboxen 569 | 11 |

COMPARATIVE EXAMPLE 8

A sample of the Sigma 4A molecular sieve as used in Comparative Example 6 was dried in a chamber furnace at 300° C. for 6 h under nitrogen (200 ml/min). 0.5000 g of the dried absorbent was then placed into a pressure vessel containing a magnetic stirrer bar. Approximately 17 g HFC-152a was added to the pressure vessel, which was sealed and stirred at 1000 rpm for 6 hours.

The supplied HFC-152a was in Comparative Example 8 found to have a methyl chloride concentration of 24 ppm. The residual quantity of methyl chloride in the remaining HFC-152a was measured by gas chromatography and was found to be 22 ppm.

Accordingly, it appears that carbon molecular sieve adsorbents may be used to selectively remove halogenated hydrocarbon impurities from (hydro)halocarbons. In particular, it appears that carbon molecular sieves may be unexpectedly adept at separating molecules which are of very similar effective diameters. Without wishing to be bound by any particular theory, it appears that the separation activity of carbon molecular sieves is based on more than simply size exclusion; it is postulated that surface interactions between the carbon molecular sieve and the composition to be separated may also play a part in the ability of the sieve to absorb some molecules into pores of restricted dimensions.

Preferences and options for a given aspect, feature or parameter of the invention should, unless the context indicates otherwise, be regarded as having been disclosed in combination with any and all preferences and options for all other aspects, features and parameters of the invention.

The invention claimed is:

1. A process for treating a composition comprising 1,1-difluoroethane and one or more undesired halogenated hydrocarbon containing impurities so as to reduce the concentration of at least one undesired halogenated hydrocarbon containing impurity,
    wherein the undesired halogenated hydrocarbon containing impurities comprises one or more of a mono-, di- or tri-halomethane,
    wherein the process comprises contacting the composition with an adsorbent comprising a carbon molecular sieve.

2. The process according to claim 1, wherein the contacting step is performed, at least in part, at a temperature of less than about 200° C.

3. The process according to claim 1, wherein the contacting step is performed, at least in part, at a temperature of about 20° C. to about 100° C.

4. The process according to claim 1, wherein the contacting step is performed at a temperature of from about 5° C. to about 200° C.

5. The process according to claim 1, wherein the process is performed, at least in part, at a temperature of about 20° C. to about 60° C.

6. The process according to claim 5, wherein the process is performed, at least in part, at a temperature of around 40° C.

7. The process according to claim 1 wherein the contacting step is conducted at a pressure of from 0.1 MPa to the saturation pressure.

8. The process according to claim 1 further comprising an adsorbent treatment step prior to the contacting step.

9. The process according to claim 8, wherein the adsorbent treatment step comprises an exposure step comprising exposing the adsorbent to Na or one or more noble gases.

10. The process according to claim 8, wherein the adsorbent treatment step comprises a heat treatment step comprising heating the adsorbent to a maximum temperature of at least 150° C.

11. The process according to claim 10, wherein the heat treatment step is carried out at a temperature at least 200° C.

12. The process according to claim 10, wherein the heat treatment step is carried out at a temperature at least 250° C.

13. The process according to claim 10, wherein the heat treatment step is carried out at a temperature at least 300° C.

14. The process according to claim 10, wherein the heat treatment step is carried out at a temperature at least 350° C.

15. The process according to claim 10, wherein the heat treatment step is carried out at a temperature at least 400° C.

16. The process according to claim 10, wherein the heat treatment step comprises heating the adsorbent to the maximum temperature at a rate of 1° C./min to 100° C./min.

17. The process according to claim 16, wherein the heat treatment step comprises heating the adsorbent to the maximum temperature at a rate of 10° C./min to 60° C./min.

18. The process according to claim 16, wherein the heat treatment step comprises heating the adsorbent to the maximum temperature at a rate of 15° C./min to 40° C./min.

19. The process according to claim 10, wherein the heat treatment step comprises maintaining the adsorbent at or around a maximum temperature for between 1 second and 1 hour.

20. The process according to claim 10, wherein the adsorbent treatment step comprises an exposure step comprising exposing the adsorbent to one or more inert gases.

21. The process according to claim 20 the exposure step is performed before, during or after the heat treatment step.

22. The process according to claim 1, wherein the adsorbent has a mean pore diameter of less than around 20 Å.

23. The process according to claim 1, wherein the adsorbent has a mean pore diameter of from around 0.5 Å to around 20 Å.

24. The process according to claim 1, wherein the process removes at least 50% by weight of the halogenated hydrocarbon impurities.

25. The process according to claim 1, wherein the process removes at least 90% by weight of the halogenated hydrocarbon impurities.

26. The process according to claim 1, wherein the undesired halogenated hydrocarbons removed using the process are selected from the group consisting of chlorofluoromethanes.

27. The process according to claim 1, wherein the undesired halogenated hydrocarbons removed using the process are selected from the group consisting of chlorodifluoromethane (R-22), chlorofluoromethane (R-31), mono-, di- or trifluoromethane and mono-, di- or trichloromethane.

28. The process according to claim 1, wherein the adsorbent is dried before use.

29. The process according to claim 1, wherein the moisture content of the adsorbent is less than about 1.5% by weight.

30. The process according to claim 1, wherein the process is conducted by circulating the composition to be treated through a polishing bed containing the adsorbent.

31. The process according to claim 30, wherein the polishing bed comprises a packed or fluidised bed.

32. The process according to claim 1, further comprising a step of regenerating the adsorbent after it has been contacted with the (hydro)halocarbon composition.

33. The process according to claim 32, wherein the regenerating step comprises contacting the adsorbent with a heated nitrogen stream and/or heating the adsorbent whilst nitrogen is passed over it.

34. The process according to claim 1, wherein the composition to be treated is contacted with the adsorbent more than once.

35. The process according to claim 34, wherein, the composition is subjected to repeated contacts with one type of adsorbent or subjected to contacts with more than one type of adsorbent.

36. The process according to claim 1, further comprising one or more additional purifying steps, which may be conducted before and/or after the contacting step.

37. The process according to claim 36, wherein the additional purifying step includes treatment with one or more other molecular sieves which are preferably acid stable molecular sieves and preferably have a pore size of from 2 to 10 Å.

38. The process according to claim 36, wherein the additional purifying step comprises the use of drying agents and/or distillation techniques.

* * * * *